(12) United States Patent
Koyama et al.

(10) Patent No.: US 10,012,225 B2
(45) Date of Patent: Jul. 3, 2018

(54) TUBING PUMP

(71) Applicants: Adamant Namiki Precision Jewel Co., Ltd., Tokyo (JP); Namiki Precision Singapore Pte. Ltd., Singapore (SG)

(72) Inventors: Masahiro Koyama, Tokyo (JP); Shouta Nakamura, Tokyo (JP); Makoto Kashiwagi, Tokyo (JP); Hiroyuki Kogure, Tokyo (JP); Hiroyuki Tajima, Tokyo (JP)

(73) Assignees: Adamant Namiki Preccision Jewel Co., Ltd., Tokyo (JP); NAMIKI PRECISION SINGAPORE PTE. LTD., Singapore (SG)

( * ) Notice: Subject to any disclaimer, the term of this patent is extended or adjusted under 35 U.S.C. 154(b) by 431 days.

(21) Appl. No.: 14/443,057

(22) PCT Filed: Nov. 14, 2013

(86) PCT No.: PCT/JP2013/080765
§ 371 (c)(1),
(2) Date: May 14, 2015

(87) PCT Pub. No.: WO2014/077308
PCT Pub. Date: May 22, 2014

(65) Prior Publication Data
US 2015/0275887 A1 Oct. 1, 2015

(30) Foreign Application Priority Data
Nov. 14, 2012 (JP) .................................. 2012-250349

(51) Int. Cl.
*F04B 43/12* (2006.01)
*F04B 43/08* (2006.01)
(Continued)

(52) U.S. Cl.
CPC ......... *F04B 43/12* (2013.01); *A61M 5/14228* (2013.01); *F04B 43/0072* (2013.01);
(Continued)

(58) Field of Classification Search
CPC .. F04B 43/1253; F04B 43/0072; F04B 43/08; F04B 43/082; F04B 43/12;
(Continued)

(56) References Cited

U.S. PATENT DOCUMENTS 2,584,372 A * 2/1952 Enoch ................... E05F 1/1276
16/289
3,187,374 A * 6/1965 Lundell ................. A45C 13/34
16/289

(Continued)

FOREIGN PATENT DOCUMENTS

JP S56-045616 Y2 10/1986
JP H07-063235 A 3/1995
(Continued)

OTHER PUBLICATIONS

International Search Report; PCT/JP2013/080765; dated Feb. 18, 2014.
(Continued)

*Primary Examiner* — Dominick L Plakkoottam
*Assistant Examiner* — Benjamin Doyle
(74) *Attorney, Agent, or Firm* — Studebaker & Brackett PC

(57) ABSTRACT

A tubing pump for transferring a fluid in a detachably attached tube 30 by a pump mechanism 50, the tubing pump is equipped with: a pump body 10 having a base 11 to and from which the tube 30 can be attached and detached; a door 20 pivotally supported to be rotatable with respect to the pump body 10, so as to open or close the base 11; switching urging unit A for urging the door 20 in an opening direction
(Continued)

in a first rotation range R1 on a completely opened side and switching an urging direction to a closing direction in a second rotation range R2 on a completely closed side; and closing suppression unit B for suppressing an urging force in the closing direction by the switching urging unit A in the second rotation range R2.

9 Claims, 9 Drawing Sheets

(51) Int. Cl.
    *A61M 5/142*         (2006.01)
    *F04B 43/00*         (2006.01)
    *A61M 39/28*         (2006.01)

(52) U.S. Cl.
    CPC ............ *F04B 43/08* (2013.01); *F04B 43/082* (2013.01); *A61M 39/281* (2013.01)

(58) Field of Classification Search
    CPC ............ F04B 43/0081; F04B 43/0009; A61M 5/14228; A61M 39/281
    USPC ...... 417/474, 478, 479, 477.2; 604/151, 153
    See application file for complete search history.

(56) References Cited

U.S. PATENT DOCUMENTS

| | | | | |
|---|---|---|---|---|
| 3,354,499 A * | 11/1967 | Anderson | ............. | E05F 1/1261 16/289 |
| 3,771,194 A * | 11/1973 | Little | ............. | E05F 1/1261 16/289 |
| 3,906,587 A * | 9/1975 | Little | ............. | E05F 1/1261 16/289 |
| 3,999,245 A * | 12/1976 | Bue | ............. | A47C 17/40 16/289 |
| 4,091,502 A * | 5/1978 | Little | ............. | E05D 11/1064 16/273 |
| 4,520,977 A * | 6/1985 | Holzhauser | ............. | G03B 27/6207 16/306 |
| 4,654,930 A * | 4/1987 | Lautenschlager, Jr. | ............. | E05D 11/1021 16/288 |
| 4,658,473 A * | 4/1987 | Schema | ............. | E05F 1/1261 16/286 |
| 4,947,516 A * | 8/1990 | Kretchman | ............. | D06F 39/14 16/289 |
| 4,972,546 A * | 11/1990 | Lautenschlager, Jr. | ............. | E05D 11/1021 16/288 |
| 5,630,710 A * | 5/1997 | Tune | ............. | A61M 5/172 417/326 |
| 5,658,133 A * | 8/1997 | Anderson | ............. | A61M 5/172 417/479 |
| 6,158,088 A * | 12/2000 | Bulboaca | ............. | B64G 1/222 16/291 |
| 6,629,955 B2 * | 10/2003 | Morris | ............. | A61M 5/14228 417/234 |
| 7,178,202 B2 * | 2/2007 | Hirtsiefer | ............. | E05D 3/14 16/286 |
| 7,367,376 B2 * | 5/2008 | Llagostera Forns | ............. | E04F 10/0611 160/66 |
| 7,418,766 B2 * | 9/2008 | Nelson | ............. | E05D 11/1007 16/239 |
| 7,500,287 B2 * | 3/2009 | Brustle | ............. | E05F 1/1075 16/286 |
| 9,217,428 B2 * | 12/2015 | Koyama | ............. | F04B 45/08 |
| 9,415,911 B2 * | 8/2016 | Schaefer | ............. | B65D 51/00 |
| 2003/0181865 A1 * | 9/2003 | Abrahamson | ......... | F04B 43/082 604/250 |
| 2007/0270765 A1 * | 11/2007 | Hasler | ............. | A61M 5/14228 604/246 |
| 2009/0241290 A1 * | 10/2009 | Jones | ............. | B41J 3/4071 16/291 |
| 2009/0306592 A1 * | 12/2009 | Kasai | ............. | A61M 5/14228 604/131 |
| 2014/0003985 A1 * | 1/2014 | Schaefer | ............. | B65D 51/00 417/476 |
| 2014/0219843 A1 * | 8/2014 | Koyama | ............. | F04B 45/08 417/477.3 |
| 2015/0275887 A1 * | 10/2015 | Koyama | ............. | F04B 43/08 417/476 |

FOREIGN PATENT DOCUMENTS

| | | | |
|---|---|---|---|
| JP | 2004-146580 A | | 5/2004 |
| JP | 2008-190333 A | | 8/2008 |
| JP | 2008190333 | * | 8/2008 |

OTHER PUBLICATIONS

The extended European search report issued by the European Patent Office dated Sep. 19, 2016, which corresponds to European Patent Application No. 13855928.1-1608 and is related to U.S. Appl. No. 14/443,057.

* cited by examiner

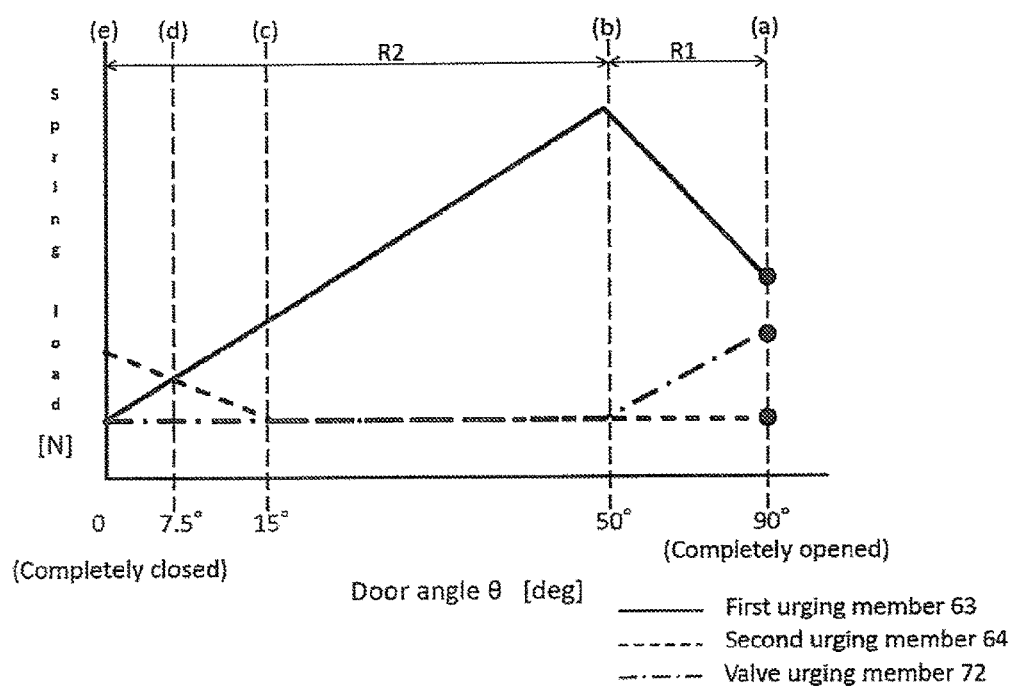

TUBING PUMP

TECHNICAL FIELD

The invention relates to a tubing pump for transferring a fluid in a detachably attached tube by a pump mechanism.

BACKGROUND ART

Conventionally, as described in Patent Document 1, this type of the invention includes: a pump body (10) to and from which a transfusion tube (40) can be attached and detached; a door (door unit 20) pivotally supported to open or close a base of the pump body (10); and a handle (23) for closing valves (14A, 14B) of a pump mechanism by a lever operation that follows a closing operation of the door.

According to this background art, the transfusion tube (40) is attached to the pump body (10), and the door (door unit 20) is closed. Then, when the handle (23) rotates, the valves (14A, 14B) of the pump mechanism are automatically closed. Accordingly, it is possible to prevent an unintentional flow of a medical fluid or the like in the transfusion tube (40) that is caused by gravity, vibration, or the like.

By the way, regarding such a tubing pump, a configuration that the door is rotated by an electric motor, a configuration that manual opening or closing of the door is assisted by an urging force of a spring, and the like are suggested to further improve opening and closing operability of the door.

However, part cost tends to be increased in the former case due to use of the electric motor, a gear, a switch, and the like. Meanwhile, in the latter case, low cost production can be expected when compared to the case where the electric motor is used. However, when the spring is too weak, a sufficient assisting force cannot be obtained. When the spring is too strong, a shock that is generated when the door is completely closed is too large. Thus, exercise of ingenuity is required.

CITATION LIST

Patent Literatures

Patent Document 1: Japanese Domestic Re-publication of PCT International Publication No. WO2009/133705 A

SUMMARY OF THE INVENTION

Problems to be Solved by the Invention

The invention has been made in view of the above conventional situation and therefore has a problem of providing a tubing pump that can improve opening and closing operability of a door.

Solutions to the Problems

An unit for solving the above problem is a tubing pump for transferring a fluid in a detachably attached tube by a pump mechanism, the tubing pump being equipped with: a pump body having a base to and from which the tube can be attached and detached; a door pivotally supported to be rotatable with respect to the pump body, so as to open or close the base; switching urging unit for urging the door in an opening direction in a first rotation range on a completely opened side and switching an urging direction to a closing direction in a second rotation range on a completely closed side; and closing suppression unit for suppressing an urging force in the closing direction by the switching urging unit in the second rotation range.

Effects of the Invention

The invention is configured as described above and thus can achieve a purpose of improving opening and closing operability of a door.

BRIEF DESCRIPTION OF THE DRAWINGS

FIG. 9 is a graph for indicating a relationship between a door angle and a spring load of each urging member in the tubing pump, in which a solid line represents a first urging member, a broken line represents a second urging member, and a dashed dotted line represents a valve urging member.

DESCRIPTION OF EMBODIMENTS

Figure 1:
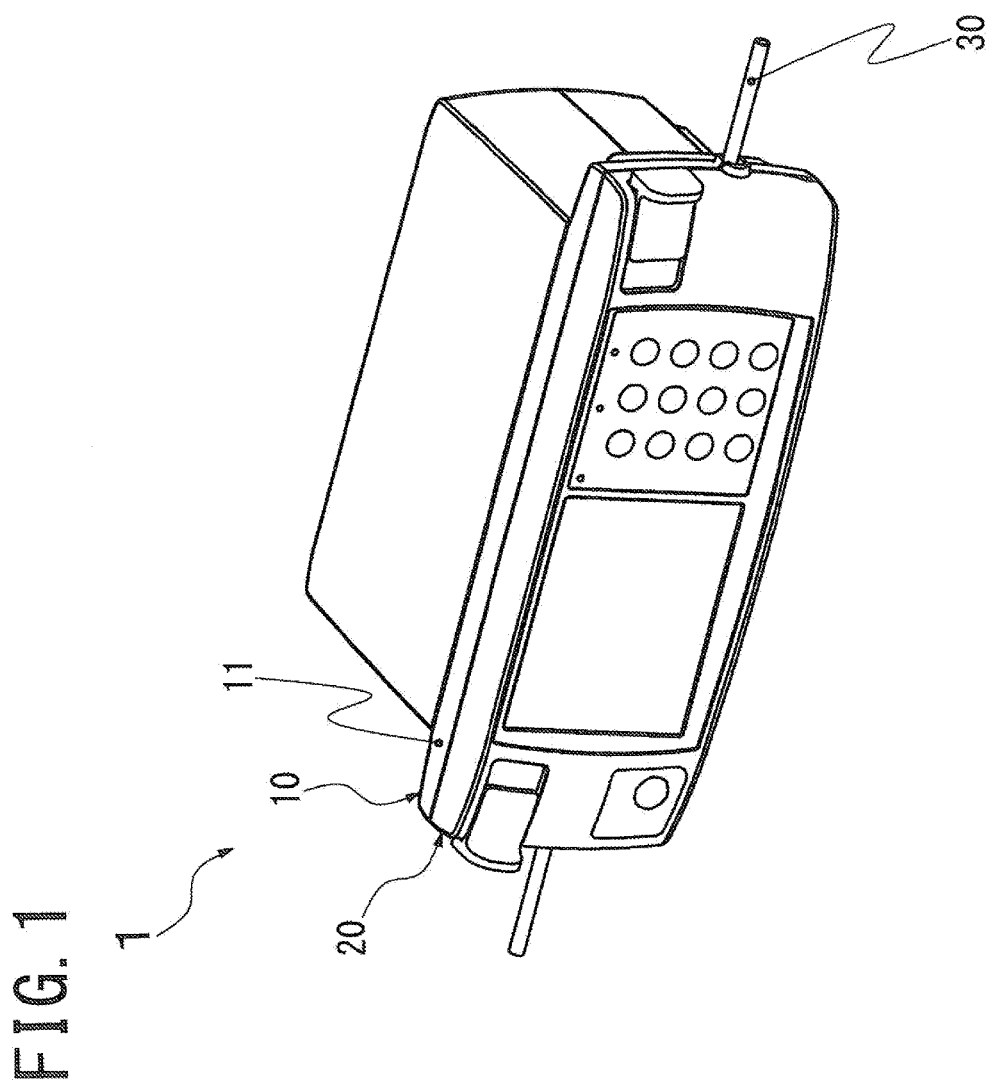
FIG. 1 is a perspective view of an example of a tubing pump according to the invention.

A first characteristic of this embodiment is a tubing pump for transferring a fluid in a detachably attached tube by a pump mechanism, the tubing pump being equipped with: a pump body having a base to and from which the tube can be attached and detached; a door pivotally supported to be rotatable with respect to the pump body, so as to open or close the base; switching urging unit for urging the door in an opening direction in a first rotation range on a completely opened side and switching an urging direction to a closing direction in a second rotation range on a completely closed side; and closing suppression unit for suppressing an urging force in the closing direction by the switching urging unit in the second rotation range.

According to this configuration, since the door is urged to the completely opened side by the switching urging unit in the first rotation range, it is possible to avoid such a situation where the door is stopped at an intermediate position between a opened position and a closed position and thus becomes an obstacle to attachment or detachment of the tube. In addition, when the door enters the second rotation range during a closing operation of the door, a direction of the urging force by the switching urging unit is switched from the opening direction to the closing direction, so as to assist in the closing operation of the door. Since the urging force at this time is suppressed by the closing suppression unit, a shock that is generated when the door is completely closed can be alleviated. As a result, a pain felt by a person whose finger or the like is stuck between the door and the pump body can be avoided.

As a second characteristic, the closing suppression unit is provided not to suppress the urging force in the closing direction by the switching urging unit in a specified range on the completely opened side within the second rotation range but to suppress the urging force in the closing direction by the switching urging unit in a specified range on the completely closed side within the second rotation range.

According to this configuration, when the door enters the second rotation range during the closing operation of the door, the door is applied with the urging force in the closing direction by the switching urging unit. Thus, the closing operation of the door can be smoothly performed. Then, when the door enters the specified range on the completely closed side within the second rotation range, the urging force in the closing direction by the switching urging unit is suppressed. In this way, an assisting force in the closing direction for the door can be reduced. Therefore, the shock that is generated when the door is completely closed can be alleviated.

As a third characteristic, the switching urging unit includes: a rod; a rod support portion that supports the rod rotatably with respect to the pump body and slidably longitudinal direction of the rod; and an urging member that urges the rod to one side in the longitudinal direction. This switching urging unit causes a front end side of the rod to be engaged with the door, so as to urge one side portion with a rotation center of the door being a boundary by one end side of the rod to perform an opening operation when the door is positioned in the first rotation range, and to rotate the rod in conjunction with a closing operation and urge another side portion with the rotation center of the door being the boundary by the one end side of the rod to perform the closing operation of the door when the closing operation is performed until the door is positioned in the second rotation range.

According to this configuration, when the door is positioned in the first rotation range, the one end side of the rod is positioned in the one side portion of the door with the rotation center being the boundary. For this reason, the one side portion is urged by the one end side of the rod, and thus the door is operated in the opening direction.

Meanwhile, when the closing operation is performed until the door is positioned in the second rotation range, the rod rotates about the rod support portion in conjunction with the closing operation, and the one end side of the rod moves to the other side portion of the door with the rotation center being the boundary. For this reason, the other side portion is urged by the one end side of the rod, and thus the door is operated in the closing direction.

As a fourth characteristic, the switching urging unit is equipped with a first urging member as the urging member on a portion of the rod on a front side of the rod support portion. The closing suppression unit is equipped with a second urging member for urging the rod to the rear on a portion of the rod on a rear side of the rod support portion.

According to this configuration, the switching urging unit and the closing suppression unit are respectively disposed in front and rear portions of the same rod. Therefore, structures of these components can be an integrated structure while a space therefor is saved.

As a fifth characteristic, the rod is urged to the front by the first urging member and urged to the rear by the second urging member in a range on a completely closed side of a specified angle within the second rotation range. A load of the second urging member is maintained to be substantially constant by the rod that slides to the rear in a range on a completely opened side of the specified angle.

According to this configuration, an influence of the load of the second urging member is insignificant in the range on the completely opened side of the specified angle, and only a load of the first urging member in accordance with a door angle acts on a hand or the like that operates the door. Therefore, favorable operability can be obtained.

As a sixth characteristic, the pump mechanism includes a valve mechanism that presses and deforms the attached tube in a radial direction by using an urging force of a valve urging member, so as to close the valve, and is configured to open this valve mechanism when the fluid is transferred into the tube. The valve mechanism is provided to be pressed and opened by the one end side of the rod that rotates in conjunction with the opening operation when this opening operation of the door is performed, and to separate from the one end side of the rod and be maintained in a closed state by the urging force of the valve urging member when the closing operation of the door is performed.

According to this configuration, when the opening operation of the door is performed, the valve mechanism is pressed and opened by the one end side of the rod that rotates in conjunction with this opening operation. Thus, the tube can be removed from the pump mechanism in this state.

Meanwhile, when the closing operation of the door is performed, the valve mechanism separates from the one end side of the rod, and the valve mechanism is maintained in the closed state by the urging force of the valve urging member. Thus, in this state, activation of the pump mechanism can be waited while a flow of the fluid in the tube caused by gravity, vibration, or the like is inhibited.

Next, a preferred example that embodies the above aspect will be described in detail on the basis of the drawings.

EXAMPLE

A tubing pump 1 according to the invention causes a fluid (for example, a medical fluid or a nutritional supplement) to forcibly flow in a tube by the pump, so as to inject the fluid into a patient body (see FIG. 1).

Figure 2:
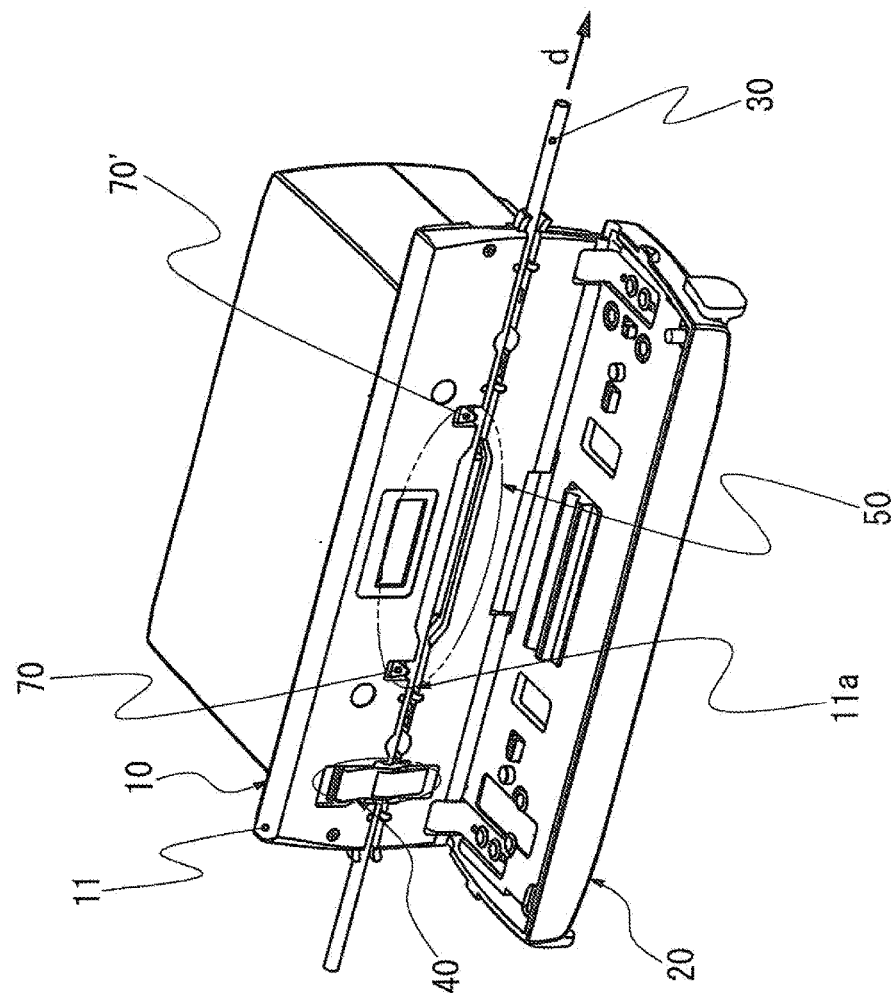
FIG. 2 is a perspective view of a state that a door is opened in the tubing pump.
Figure 3:
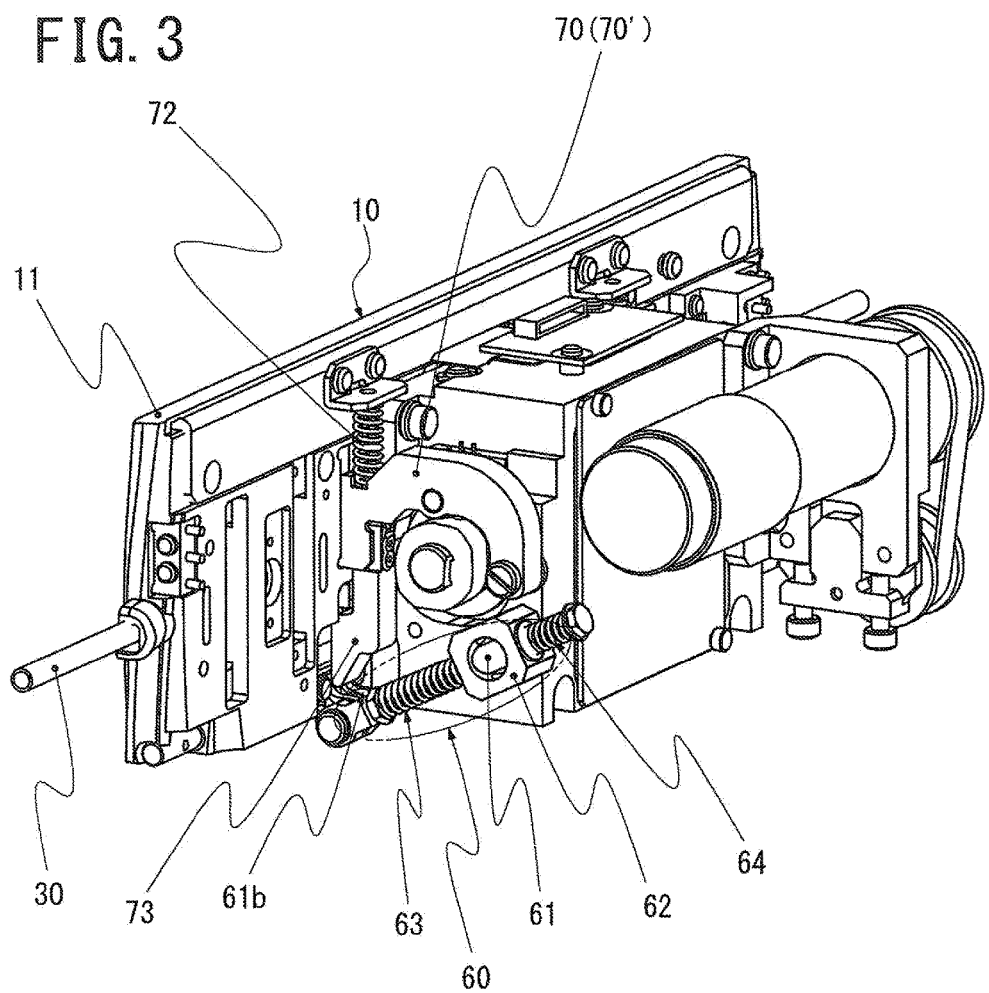
FIG. 3 is a perspective view of a main portion of the tubing pump that is seen obliquely from a rear side.

This tubing pump 1 is equipped with: a pump body 10; a door 20 that opens or closes a base 11 as a front part of the pump body 10; a tube 30 and a clamp device 40 that are detachably attached to the base 11; a pump mechanism 50 that is provided in the base 11 and transfers the fluid in the tube 30; and an opening and closing assist mechanism 60 that assists in opening or closing of the door 20 (see FIGS. 1 to 3).

The pump body 10 is formed in a substantially rectangular box shape and has the vertically-arranged base 11 on a front side thereof that is opened or closed by the door 20. The tube 30 is transversely inserted through this base 11 (see FIGS. 1 to 3).

The base 11 is a substantially thick plate-shaped portion, and a front part thereof is equipped with a horizontal groove for attaching or detaching the tube 30, a recessed portion for attaching or detaching the clamp device 40, the pump mechanism 50 for forcibly transferring the fluid in the attached tube 30, and the like.

A shaft 11b (see FIG. 4) that rotatably supports the door 20 is provided on a lower end side of the base 11. This shaft 11b is a columnar or cylindrical shaft that is fixed to a recessed portion on the lower end side of the base 11 in a manner incapable of rotating in the substantially horizontal direction.

The door 20 is a substantially plate-shaped member that is pivotally supported to be rotatable on the lower end side of the base 11, is closed to cover the substantially perpendicular front part of the base 11, and opens the same portion. When this door 20 is closed and superimposed on the front part of the base 11, so as to be completely closed, a closed state thereof is retained by a catch mechanism (not depicted) that is provided between the base 11 and the door 20. The catch mechanism may be, for example, a mechanism that locks a locking portion on the door 20 side to a locked portion on the base 11 side by using an urging force of an urging member and cancels the locking by a lever operation or a mechanism that detachably suctions the door 20 and the base 11 by a magnet.

A rotation base 21 (see FIGS. 4 to 8) is provided on a lower end side of the door 20. The rotation base 21 is annularly attached to the shaft 11b of the base 11 so as to rotate in a freely rotatable manner, and is engaged with the opening and closing assist mechanism 60, which will be described below.

According to a depicted example, this rotation base 21 is formed in a substantially cylindrical shape, a portion of an outer peripheral surface thereof is fixed to the lower end side of the door 20, and another portion of the outer peripheral surface thereof pivotally supports a tip of a rod 61 of the opening and closing assist mechanism 60 to be rotatable.

The tube 30 is a circular tube that is made of a transparent synthetic resin, is deformed and closed when being squished by a pressing force in a radial direction, and elastically restores an original shape when the pressing force is canceled.

The clamp device 40 is configured to hold and deform the tube 30 in the radial direction, so as to close the tube 30 in a state of being attached to the tube 30, and to cancel the closed state when a specified operation (for example, a closing operation of the door 20 or the unillustrated lever operation) is performed in a state of being attached to the base 11 together with the tube 30.

For example, as disclosed in JP-A-2007-23803 and Japanese Domestic Re-publication of PCT International Publication No. WO 2009/133705 A, the pump mechanism 50 forcibly transfers the fluid in the tube 30 in a d-direction that is indicated by an arrow in FIG. 2 by appropriately combining pressing and releasing operations of the attached tube 30, opening and closing operations of a valve mechanism 70 on an upstream side thereof, opening and closing operations of a valve mechanism 70' on a downstream side thereof, and the like (see FIG. 2).

In addition, the opening and closing assist mechanism 60 is a mechanism that is supported by the pump body 10 on a rear portion side (back side) of the base 11, and is equipped with: the rod 61; a rod support portion 62 that supports the rod 61 rotatably with respect to the pump body 10 and slidably in a longitudinal direction of the rod; a first urging member 63 that urges the rod 61 to the front; and a second urging member 64 that urges the rod 61 to the rear in a portion of the rod 61 on a rear side of the rod support portion 62 (see FIGS. 3 to 8).

Then, in this opening and closing assist mechanism 60, a configuration thereof on a front side of the rod support portion 62 constitutes switching urging unit A that urges the door 20 in an opening direction in a first rotation range R1 on a completely opened side and that switches an urging direction to a closing direction in a second rotation range R2 on a completely closed side, and a configuration thereof on the rear side of the rod support portion 62 constitutes closing suppression unit B that suppresses an urging force in the closing direction by the switching urging unit A in the second rotation range R2.

The rod 61 is a shaft-shaped member that extends in a front-rear direction on the back side of the base 11, and is supported by the rod support portion 62 so as to freely advance or retreat in the front-rear direction and to freely rotate about the rod support portion 62.

A portion (an engaged and disengaged portion 61b, which will be described below) on a front end side (right end side in FIG. 4) of this rod 61 is rotatably connected to the outer peripheral surface of the rotation base 21 of the door 20 via a hinge or the like. Accordingly, when the rotation base 21 of the door 20 rotates in conjunction with the opening and closing operations of the door 20, the front end of the rod 61 is pulled by an outer periphery of the rotation base 21 and also rotates around the rotation base 21 by tracing a substantially fan-shaped path (see FIGS. 4 to 8).

The rod support portion 62 is a cylindrical member that is arranged substantially parallel to the rotation base 21 of the door 20 and rotatably supported with respect to the pump body 10. The rod 61 is inserted through a peripheral wall thereof so as to slide in the front-rear direction.

The engaged and disengaged portion 61b that is engaged and disengaged with and from the valve mechanism 70 (or the valve mechanism 70') is formed on the front end side of this rod support portion 62. This engaged and disengaged portion 61b is formed on an outer peripheral surface in a semi-columnar shape so as to receive the valve mechanism 70 (see FIGS. 4 to 8).

It should be noted that an aspect in which, as the engaged and disengaged portion 61b, a ball bearing is arranged on the front end side of the rod support portion 62 can also be adopted.

The first urging member 63 is a compression coil spring, is annularly attached to the portion of the rod 61 on the front side of the rod support portion 62, has one seat thereof that abuts against the outer periphery of the rod support portion 62 and another seat that is received by a step 61a on the front end side of the rod 61, and urges the rod 61 to the front.

The second urging member 64 is a compression coil spring, is annularly attached to the portion of the rod 61 on the rear side of the rod support portion 62, has one seat that abuts against the outer periphery of the rod support portion 62 and another seat that is received by a nut 61c screwed to a rear end side of the rod 61, and urges the rod 61 to the rear.

It should be noted that a plain washer or the like for adjusting a spring load is interposed as a spacer on the front or the rear of the first urging member 63 and/or on the front or the rear of the second urging member 64 if necessary.

In addition, the valve mechanisms 70, 70' are configured to press and deform the attached tube 30 in the radial direction by using an urging force of a valve urging member 72 for closing and to open the tube 30 when the fluid is transferred thereinto.

As will be described further in detail, as depicted in FIG. 2, the valve mechanism 70 is arranged on the upstream side of the tube 30, is pressed and opened by the front end side of the rod 61 that rotates in conjunction with an opening operation of the door 20 when this opening operation is performed, and separates from the front end side of the rod 61 and is maintained in a closed state by the urging force of the valve urging member 72 when the closing operation of the door 20 is performed.

This valve mechanism 70 is equipped with: a tube placing surface 11a in the base 11; a holding member 71 that holds the tube 30 between the tube placing surface 11a and the holding member 71; the valve urging member 72 that urges the holding member 71 in a holding direction; and a transmission member 73 that is integrally constructed with the holding member 71 and transmits motion of the rod 61 to the holding member 71.

The tube placing surface 11a is a lower surface of the groove, through which the tube 30 is inserted, in the base 11 and receives the tube 30, which is attached to the base 11, from a lower side.

The holding member 71 is constructed of a base piece 71a that is pivotally supported to be rotatable with respect to the pump body 10 and a pressing piece 71b that is connected to a tip side of the base piece 71a and presses the tube 30 from above.

The base piece 71a is supported to rotate with respect to the pump body 10 via a shaft 71c that is substantially parallel to the tube 30 in the attached state, and is urged downward by the valve urging member 72 from an upper side while a rotation end side thereof faces the base 11.

The pressing piece 71b is integrally fixed to the rotation end side of the base piece 71a, and is formed in a wedge shape such that a lower end side thereof is gradually thinned downward. This pressing piece 71b is arranged to face the tube placing surface 11a so as to hold the tube 30 substantially at a right angle.

In addition, the valve urging member 72 is a compression coil spring. One seat thereof is fixed to the pump body 10, and another seat thereof urges the holding member 71 in the holding direction (downward according to the depicted example).

Furthermore, the transmission member 73 has a crank shape depicted in FIGS. 4 to 8, and has: a receiving portion 73a that receives the semicircular engaged and disengaged portion 61b of the rod 61 from below; and an inclined surface 73b that receives the engaged and disengaged portion 61b obliquely from below (obliquely from below and the left according to FIG. 5) for sliding on a lower end side thereof.

The receiving portion 73a is a surface that faces an outer peripheral surface of the engaged and disengaged portion 61b of the rod 61 from the upper side.

The inclined surface 73b is an inclined surface that is connected to the receiving portion 73a via a recessed curved surface, and is formed to be pressed against and slidingly contact a tip of the engaged and disengaged portion 61b of the rod 61.

It should be noted that the other valve mechanism 70' is arranged on the downstream side of the tube 30. Since this valve mechanism 70' has a substantially similar configuration as the above valve mechanism 70, an overlapping detailed description thereof will not be made.

Next, characteristic operational effects of the tubing pump 1 with the above configuration will be described in detail.

First, in a state that the door 20 is at a completely opened position (see FIG. 4), the first urging member 63 elastically urges the rod 61 to the front (in a right direction in FIG. 4) with a larger spring load than that of the second urging member 64 and that of the valve urging member 72 (see FIG. 9).

Figure 4:
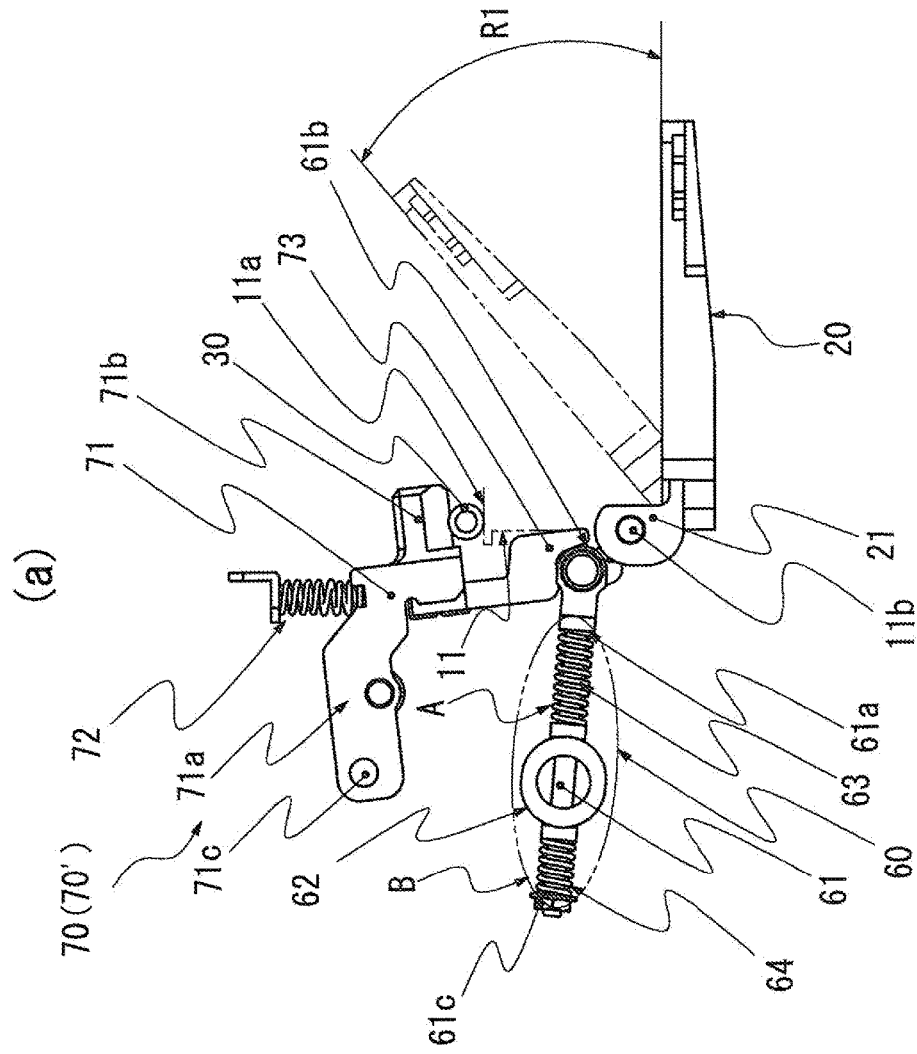
FIG. 4 is an explanatory view of an operation of the tubing pump and corresponds to a time point (a) on a graph in FIG. 9.

In this state, a center line of the rod 61 is located on one side (upper side) with a center (rotation center) of the shaft 11b being a boundary, and the rod 61 presses the outer periphery of the rotation base 21 of the door 20 (see FIG. 4). Thus, the rotation base 21 and the door 20 are urged in the opening direction. Since a portion of the door 20 abuts against an immobile portion of the base 11 or the like (not depicted), the rotation of the door 20 in the opening direction is restricted, and the door 20 is stopped at the completely opened position.

In addition, in this state, as depicted in FIG. 4, the engaged and disengaged portion 61b at the front end of the rod 61 abuts against and presses the transmission member 73 of the valve mechanism 70 from below. In this way, the valve mechanism 70 is maintained in a completely opened state. Accordingly, in some portion of the valve mechanism 70, the tube 30 is retained in an opened state in which the fluid therein can be distributed. It should be noted that a lower end side of the transmission member 73 abuts against a side surface of the base 11 in this state. Thus, rotation of the holding member 71 in the opening direction is restricted.

Figure 5:
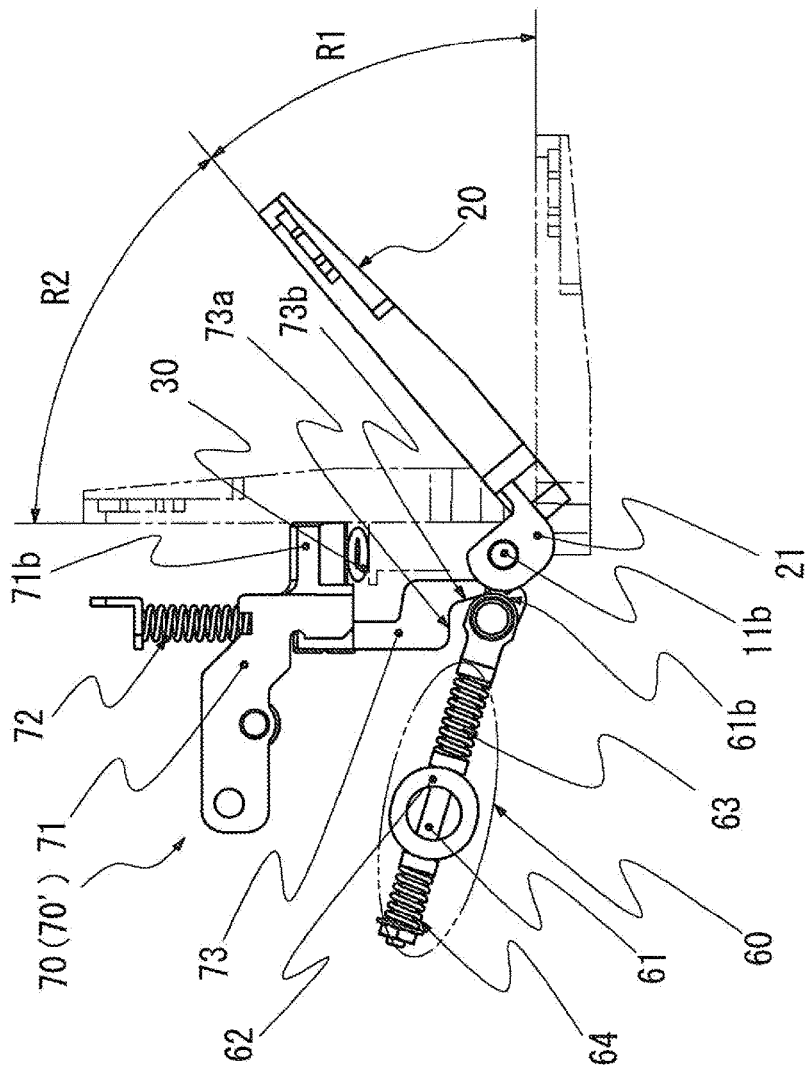
FIG. 5 is an explanatory view of the operation of the tubing pump and corresponds a time point (b) on the graph in FIG. 9.

Next, when the closing operation of the door 20 is performed, the engaged and disengaged portion 61b of the rod 61 moves in the substantially fan shape in conjunction with the closing operation such that the center line of the rod 61 approaches the center (rotation center) of the shaft 11b (see FIGS. 4 and 5). During this movement, in the first rotation range R1 in which the center line of the rod 61 does not surpass the center (rotation center) of the shaft 11b, the urging force by the holding member 71 in the opening direction of the door 20 is retained, and the urging force of the first urging member 63 is accumulated (see FIG. 9).

In addition, during the movement (in other words, during the closing operation of the door 20 on a completely opened side in the first rotation range R1), the holding member 71 rotates downward by the urging force of the valve urging member 72 in a manner to follow the downward rotation of the front end of the engaged and disengaged portion 61b at the front end of the rod 61. Accordingly, the pressing piece 71b at the front end of the holding member 71 presses and gradually closes the tube 30. Then, when the engaged and disengaged portion 61b at the front end of the rod 61 further rotates downward, as depicted in FIG. 5, the engaged and disengaged portion 61b separates from the receiving portion 73a of the transmission member 73 and moves downward while slidingly contacts the inclined surface 73b.

Furthermore, when the door 20 during the closing operation moves beyond the first rotation range R1 and enters the second rotation range R2, the engaged and disengaged portion 61b at the front end of the rod 61 completely separates from the transmission member 73. Accordingly, the holding member 71 is retained in a state of pressing and closing the tube 30 in the closed state by the urging force of the valve urging member 72 (see FIGS. 6 to 8).

During the closing operation, in the second rotation range R2, the first urging member 63 urges the rod 61 to the front while being extended, and gradually reduces the spring load thereof (see FIG. 9). In addition, in this state, the center line of the rod 61 is located on another side (a lower side) with the center (rotation center) of the shaft 11b being the boundary, and the rod 61 presses the outer periphery of the rotation base 21 of the door 20 (see FIGS. 6 to 8). Accordingly, the rotation base 21 and the door 20 are urged in the closing direction. Thus, the closing operation of the door 20 is assisted by the urging force of the first urging member 63.

Figure 6:
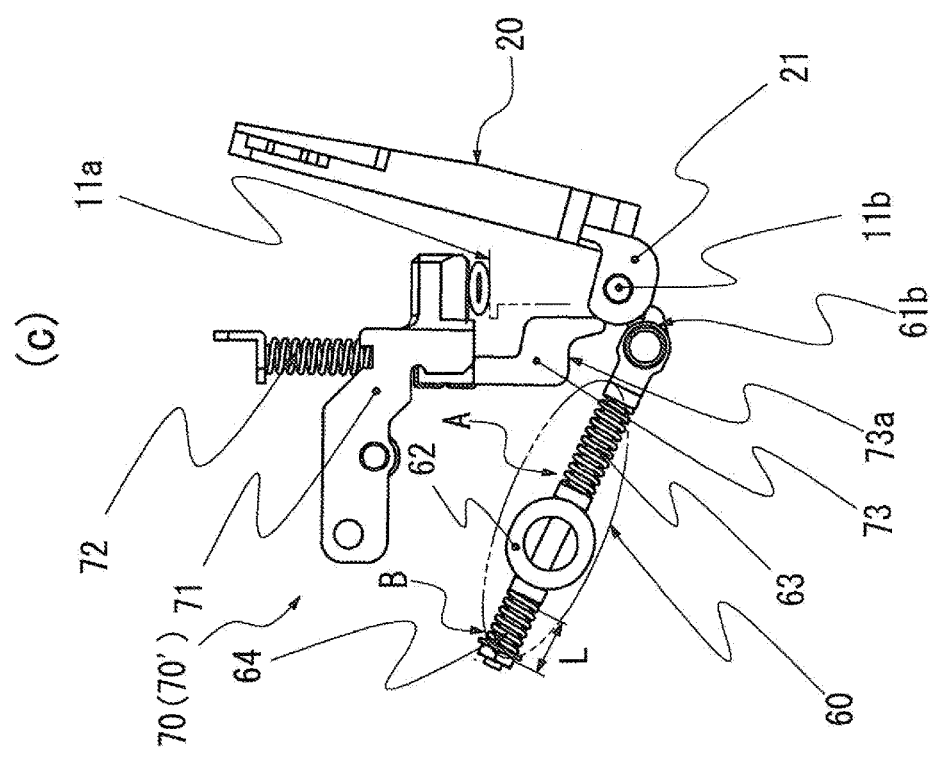
FIG. 6 is an explanatory view of the operation of the tubing pump and corresponds a time point (c) on the graph in FIG. 9.

When the closing operation of the door 20 is further performed to have a smaller angle than a specified angle (specifically, a door angle of 15° indicated in FIGS. 9 and 6(c)), a spring attachment length L (see FIG. 6) of a portion of the rod 61 on the rear side of the rod support portion 62 becomes shorter than a free length of the second urging member 64 due to forward movement of the rod 61, and the second urging member 64 accumulates the urging force while being gradually compressed (see FIG. 9).

In other words, the closing suppression unit B that is constructed of the second urging member 64 and the like does not suppress the urging force in the closing direction by the switching urging unit A in a specified range on the completely opened side within the second rotation range R2 (on the opening direction side from the door angle of 15° in the depicted example), but suppresses the urging force in the closing direction by the switching urging unit A in a specified range on the completely closed side within the second rotation range R2 (on the closing direction side from the door angle of 15° in the depicted example).

Thus, a shock generated when the door 20 is completely closed is alleviated. Therefore, damage to the tubing pump 1 by the shock, a pain felt by a person whose finger or the like is stuck between the door 20 and the base 11, and the like can be prevented.

Then, as depicted in FIG. 9, in the completely closed state of the door 20, the unillustrated catch mechanism maintains the completely closed state.

In this completely closed state, the valve mechanisms 70, 70' are each maintained in the closed state by the urging force of the valve urging member, and thus can wait for activation of the pump mechanism 50 while inhibiting the flow of the fluid in the tube 30 caused by gravity, vibration, or the like.

On the contrary, when an opening operation of the door 20 in the completely closed state is performed, the above operation is reversed. First, when the above unillustrated catch mechanism is canceled, the door 20 is slightly assisted in the opening direction by the urging force of the second urging member 64 (see a broken line from (e) to (d) in FIG. 9).

Figure 7:
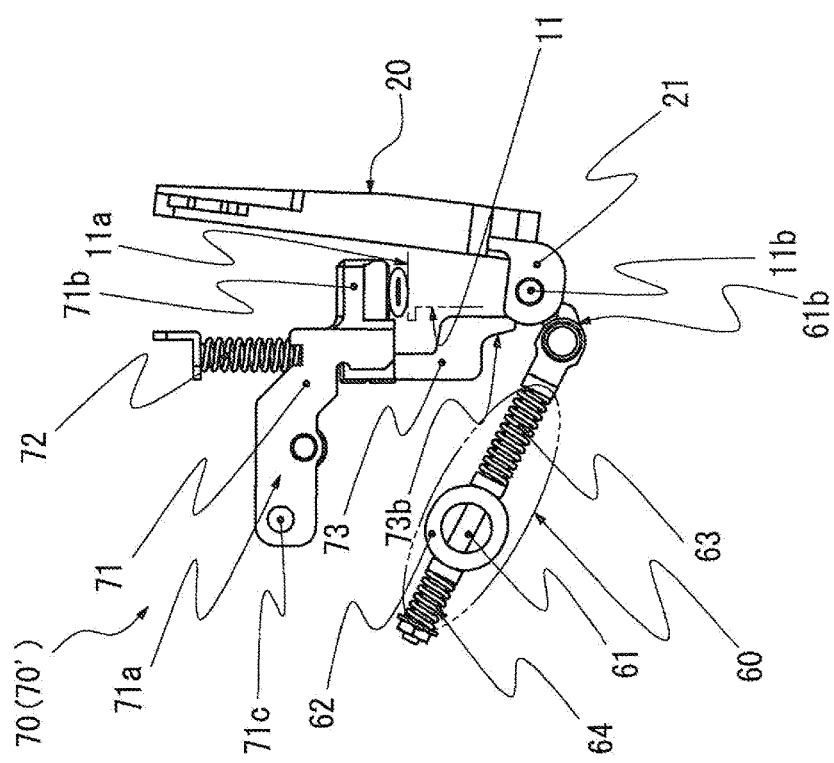
FIG. 7 is an explanatory view of the operation of the tubing pump and corresponds a time point (d) on the graph in FIG. 9.
Figure 8:
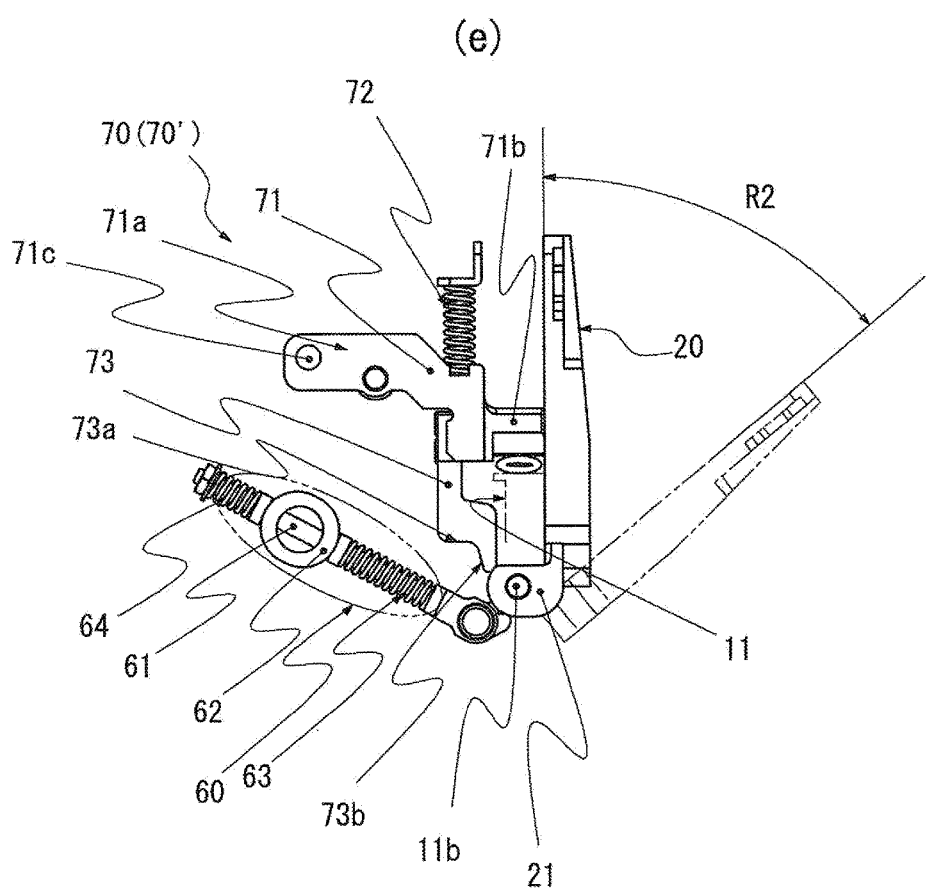
FIG. 8 is an explanatory view of the operation of the tubing pump and corresponds a time point (e) on the graph in FIG. 9.

Then, when a time point (c) indicated in FIGS. 7 and 9 is passed in the opening direction, the spring attachment length L (see FIG. 6) of the portion of the rod 61 on the rear side of the rod support portion 62 becomes longer then the free length of the second urging member 64. Accordingly, the load of the second urging member 64 is maintained to be substantially constant (for example, at zero or a value close to zero), and resistance by the first urging member 63, a degree of which corresponds to an opening amount of the door 20, is generated. The urging force of the first urging member 63 is accumulated by this opening operation.

Furthermore, when a time point (b) indicated in FIGS. 5 and 9 is passed in the opening direction, the center line of the rod 61 is located on the upper side of the center of the shaft 11$b$, and the rod 61 presses the outer periphery of the rotation base 21 of the door 20 (see FIGS. 4 and 5). Accordingly, the rotation base 21 and the door 20 are urged in the opening direction. Thus, the opening operation of the door 20 is assisted by the urging force of the first urging member 63.

Furthermore, during the opening operation, at the time point (b) indicated in FIGS. 5 and 9, the engaged and disengaged portion 61$b$ of the rod 61 abuts against the inclined surface 73$b$ of the transmission member 73. When this time point is further passed in the opening direction, due to the rotation of the rod 61 that is interlocked with the opening operation of the door 20, the engaged and disengaged portion 61$b$ causes the holding member 71 to rotate in the opening direction while slidingly contacting the inclined surface 73$b$. Then, when the opening operation of the door 20 further continues, the engaged and disengaged portion 61$b$ abuts against the receiving portion 73$a$ of the transmission member 73. Thereafter, while this abutment state is maintained, the opening operation of the door 20, the rotation of the rod 61, and the rotation of the holding member 71 are interlocked.

Then, when the tube 30 is almost completely opened by the rotation, the transmission member 73 abuts against the base 11 (see FIG. 4). In this way, the rotation becomes restricted, and the door 20 is retained in the completely opened state.

It should be noted that, according to the above example, the door 20 is at the completely opened position in a state that the angle of the door 20 with respect to the base 11 is approximately 90°. However, as other examples of this completely opened position, an aspect of a state that the angle of the door 20 with respect to the base 11 is approximately 100° and an aspect with another angle can be raised. In addition, as other examples of the first urging member 63, the second urging member 64, and the valve urging member 72, an aspect that uses a tension spring and an aspect that uses an elastic member other than the coil spring, such as rubber or a plate spring, can be raised.

In addition, according to the above example, the switching urging unit A and the closing suppression unit B are constructed of the integrated opening and closing assist mechanism 60. As another example, the switching urging unit A and the closing suppression unit B can independently be constructed.

In addition, according to the above example, the urging force in the closing direction by the switching urging unit A is suppressed by the closing suppression unit B only in the partial range of the second rotation range R2. As another example, an aspect in which the urging force in the closing direction by the switching urging unit A is suppressed by the closing suppression unit B in an entire range of the second rotation range R2 can be raised.

In addition, according to the above example, the urging force of the second urging member 64 does not act in the first rotation range R1. As another example, an aspect in which the urging force of the second urging member 64 acts in a partial or entire range of the first rotation range R1 can be raised.

In addition, according to the above example, the aspect in which the opening operation of the door 20, the rotation of the rod 61, and the rotation of the holding member 71 are interlocked at appropriate timing is adopted. As other examples, an aspect in which these are interlocked at timing that is not indicated in the example, and an aspect in which only the holding member 71 is not interlocked can be raised.

In addition, according to the above example, the door angles that correspond to those in FIGS. 4 to 8 are respectively set at (a) 90°, (b) 50°, (c) 15°, (d) 7.5°, (e) 0° as indicated in FIG. 9. However, these angles can be changed by adjusting an angle range in which the door can be opened or closed, the spring load and the attachment length of the each urging member, a positional relationship between the opening and closing assist mechanism 60 and the door 20, and the like.

LIST OF THE REFERENCE NUMERALS

1 Tubing pump
10 Pump body
11 Base
11$b$ Shaft
20 Door
21 Rotation base
30 Tube
50 Pump mechanism 60 Opening and closing assist mechanism
61 Rod
62 Rod support portion
63 First urging member
64 Second urging member
70, 70' Valve mechanism
A Switching urging unit
B Closing suppression unit
R1 First rotation range
R2 Second rotation range

The invention claimed is:

1. A tubing pump for transferring a fluid in a detachably attached tube by a pump mechanism, the tubing pump comprising:
   a pump body having a base to and from which the tube can be attached and detached;
   a door pivotally supported to be rotatable with respect to the pump body within a rotation range between a completely-closed position where the base is covered and a completely-opened position where the base is uncovered, the rotation range including a first rotation range and a second rotation range, the first rotation range being located at a completely opened position side of the second rotation range and the second rotation range being located at a completely closed position side of the first rotation range;
   a rotation base provided on one end of the door;
   a switching urging unit having a first urging member and a portion configured to press the rotation base due to an urging force of the first urging member to urge the door in an opening direction in the first rotation range and to switch an urging direction to a closing direction in the second rotation range; and
   a closing suppression unit having a second urging member to suppress the urging force of the first urging member in the closing direction by the switching urging unit in the second rotation range, wherein
   the second rotation range includes a first specified range and a second specified range, the first specified range being located on a completely-opened position side of the second specified range, the second specified range being located on a completely-closed position side of the first specified range, and
   the closing suppression unit is provided not to suppress the urging force in the closing direction by the switching urging unit in the first specified range but to suppress the urging force in the closing direction by the switching urging unit in the second specified range.

2. The tubing pump according to claim 1, wherein
   the switching urging unit includes: a rod; a rod support portion that supports the rod rotatably with respect to the pump body and slidably in a longitudinal direction of the rod; and the first urging member that urges the rod to one side in the longitudinal direction thereof, and
   the switching urging unit causes a front end side of the rod to be engaged with the door, so as to urge one side portion with a rotation center of the door being a boundary by one end side of the rod to perform an opening operation when the door is positioned in the first rotation range, and to rotate the rod in conjunction with a closing operation and urge another side portion with the rotation center of the door being the boundary by the one end side of the rod to perform the closing operation of the door when the closing operation is performed until the door is positioned in the second rotation range.

3. The tubing pump according to claim 2, wherein
   the switching urging unit is equipped with the first urging member on a portion of the rod on a front side of the rod support portion, and
   the closing suppression unit is equipped with the second urging member for urging the rod to the rear on a portion of the rod on a rear side of the rod support portion.

4. The tubing pump according to claim 3, wherein
   the rod is urged to the front by the first urging member and urged to the rear by the second urging member in a range on a completely closed side of a specified angle within the second rotation range, and
   a load of the second urging member is maintained to be constant by the rod that slides to the rear in a range on a completely opened side of the specified angle.

5. The tubing pump according to claim 1, wherein
   the pump mechanism includes a valve mechanism having a transmission member, a valve urging member, and a pressing piece, the pressing piece being configured to press and deform the attached tube by using an urging force of the valve urging member so as to close the valve mechanism, and
   the transmission member is provided to be pressed by one end side of the rod that rotates in conjunction with the opening operation when the opening operation of the door is performed so as to open the valve mechanism when the fluid is transferred into the tube, and to separate from the one end side of the rod so as to maintain the valve mechanism in a closed state by the urging force of the valve urging member when the closing operation of the door is performed.

6. The tubing pump according to claim 2, wherein
   the pump mechanism includes a valve mechanism having a transmission member, a valve urging member, and a pressing piece, the pressing piece being configured to press and deform the attached tube by using an urging force of the valve urging member so as to close the valve mechanism, and
   the transmission member is provided to be pressed by one end side of the rod that rotates in conjunction with the opening operation when the opening operation of the door is performed so as to open the valve mechanism when the fluid is transferred into the tube, and to separate from the one end side of the rod so as to maintain the valve mechanism in a closed state by the urging force of the valve urging member when the closing operation of the door is performed.

7. The tubing pump according to claim 3, wherein
   the pump mechanism includes a valve mechanism having a transmission member, a valve urging member, and a pressing piece, the pressing piece being configured to press and deform the attached tube by using an urging force of the valve urging member so as to close the valve mechanism, and
   the transmission member is provided to be pressed by one end side of the rod that rotates in conjunction with the opening operation when the opening operation of the door is performed so as to open the valve mechanism when the fluid is transferred into the tube, and to separate from the one end side of the rod so as to maintain the valve mechanism in a closed state by the urging force of the valve urging member when the closing operation of the door is performed.

8. The tubing pump according to claim 4, wherein
   the pump mechanism includes a valve mechanism having a transmission member, a valve urging member, and a pressing piece, the pressing piece being configured to press and deform the attached tube by using an urging force of the valve urging member so as to close the valve mechanism, and the transmission member is provided to be pressed by one end side of the rod that rotates in conjunction with the opening operation when the opening operation of the door is performed so as to open the valve mechanism when the fluid is transferred into the tube, and to separate from the one end side of the rod so as to maintain the valve mechanism in a closed state by the urging force of the valve urging member when the closing operation of the door is performed.

9. A tubing pump for transferring a fluid in a detachably attached tube by a pump mechanism, the tubing pump comprising: a pump body having a base to and from which the tube can be attached and detached; a door pivotally supported to be rotatable with respect to the pump body within a rotation range between a completely-closed position where the base is covered and a completely-opened position where the base is uncovered, the rotation range including a first rotation range and a second rotation range, the first rotation range being located at a completely opened position side of the second rotation range and the second rotation range being located at a completely-closed position side of the first rotation range; a switching urging unit for urging the door in an opening direction in the first rotation range and switching an urging direction to a closing direction in the second rotation range; and a closing suppression unit for suppressing an urging force in the closing direction by the switching urging unit in the second rotation range; wherein the second rotation range includes a first specified range and a second specified range, the first specified range being located on a completely-opened position side of the second specified range, the second specified range being located on a completely-closed position side of the first specified range, and the closing suppression unit is provided not to suppress the urging force in the closing direction by the switching urging unit in the first specified range but to suppress the urging force in the closing direction by the switching urging unit in the second specified range.

* * * * *